United States Patent [19]

Rozmus

[11] 4,233,720
[45] Nov. 18, 1980

[54] METHOD OF FORMING AND ULTRASONIC TESTING ARTICLES OF NEAR NET SHAPE FROM POWDER METAL

[75] Inventor: Walter J. Rozmus, Traverse City, Mich.

[73] Assignee: Kelsey-Hayes Company, Romulus, Mich.

[21] Appl. No.: 965,168

[22] Filed: Nov. 30, 1978

[51] Int. Cl.² .......................................... B23Q 17/00
[52] U.S. Cl. ...................................... 29/407; 29/420
[58] Field of Search ........................... 29/407, 420, 423, 29/424; 148/127, 128; 164/4

[56] References Cited

U.S. PATENT DOCUMENTS

| | | | |
|---|---|---|---|
| 3,741,755 | 6/1973 | Allen | 29/420 R |
| 3,866,303 | 2/1975 | Chehi | 29/423 |
| 4,094,709 | 6/1978 | Rozmus | 148/126 |

*Primary Examiner*—Lowell A. Larson
*Attorney, Agent, or Firm*—McGlynn and Milton

[57] ABSTRACT

A method for sonic testing powder metal articles made by hot isostatic pressing in a thick-walled container including the steps of preparing the composite thick-walled container and article for sonic testing by machining sonic surfaces in the exterior surface of the thick-walled container and thereafter sonic testing the article through the walls of the container.

2 Claims, 1 Drawing Figure

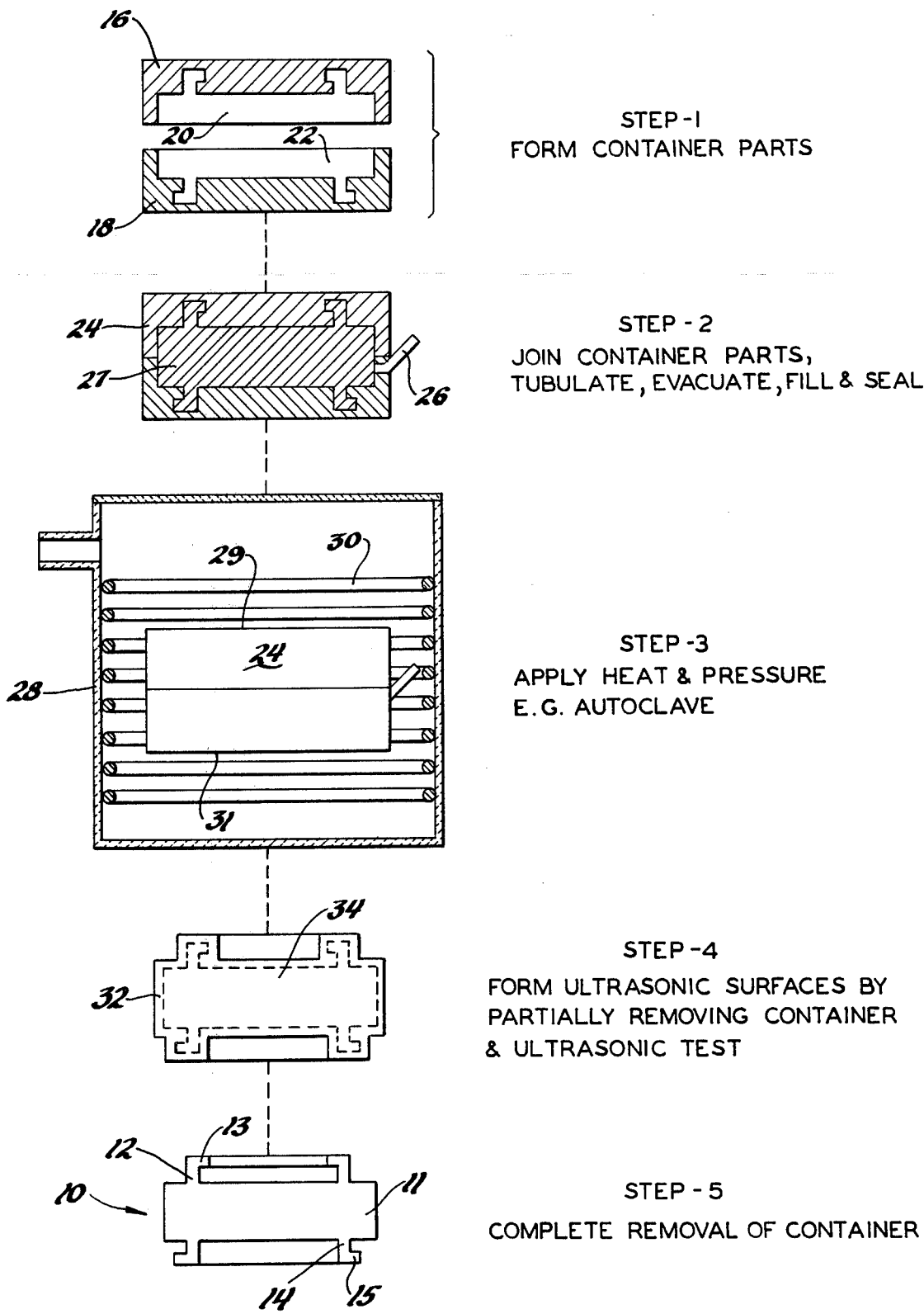

METHOD OF FORMING AND ULTRASONIC TESTING ARTICLES OF NEAR NET SHAPE FROM POWDER METAL

FIELD OF THE INVENTION

This invention relates to a method for ultrasonically testing articles of near net shape made from powder metal by hot isostatic pressing in a thick-walled container.

BACKGROUND OF THE INVENTION

The use of powder metallurgical techniques has become popular with high alloyed materials due to the problems encountered in casting such materials, e.g., segregation and the resulting loss of physical properties. For example, powder metallurigal techniques are used extensively with nickel, cobalt, and ferrous-base superalloys. These are high temperature-high strength alloys used in making turbine discs, blades, buckets, and other components of turbine engines which are subjected to high stress at mid-range or high temperatures. The very properties which make these alloys attractive for use in turbine engines cause the consolidation of the powder alloys to be difficult. Moreover, subsequent operations, such as forging and machining the resulting densified compact, to produce a final part are also difficult because of the high stength and toughness of these alloys.

Due primarily to the costs and difficulties encountered in post-consolidation processing, efforts have been made to produce "near net shapes." As used herein, a near net shape is a densified powder metal compact having a size and shape which are relatively close to the desired size and shape of the final part. Heretofore, crude performs have been produced which require extensive post-consolidation forming and machining to produce the relatively complex final part. Producing a near net shape reduces the amount of post-consolidation processing required and the amount of scrap generated. For example, in many instances subsequent hot forging can be eliminated and the amount of machining required can be significantly reduced. Since these materials are difficult to machine, a reduction in the amount of machining offers a marked savings in tool and labor costs. Additionally, these materials are quite expensive, therefore, a reduction in machining results in a savings in material costs. Obviously, eliminating or reducing the amount of hot forging also offers savings advantages.

While the desirability of producing near net shapes has been recognized, many problems have been encountered in accomplishing this objective. The basic step of consolidating the metal powder to produce a powder metal compact having a near net shape has been a major obstacle. Once an acceptable near net shape is produced, other problems are presented. One of these relates to the inspection of the near net shape by ultrasonic testing to detect flaws. One of the important uses of superalloy material is for discs and rotors in jet engines. Such components must pass stringent inspection to reduce the possibility of in-service failure. Hence, inspection of such components is an important consideration in their manufacture.

Ultrasonic testing is a well-known nondestructive testing technique for detecting the presence of flaws, particularly inclusions. In ultrasonic testing a beam of acoustical radiation having a frequency higher than the frequency of audible sound is transmitted through the object to be tested. In the simplest forms of ultrasonic testing, a continuous stream of waves is sent through the part under test. Large flaws in the part cast an acoustical shadow on the opposite face of the piece which can be detected. Ultrasonic waves can be produced and detected by piezoelectric crystals.

Smaller flaws are detected by more sophisticated ultrasonic equipment which sends a wave train into the part. Small flaws relect the waves which are detected and displayed on a cathode-ray tube or recorded by a suitable recording device.

In any ultrasonic testing procedure it is necessary to provide a smooth surface on the part. A surface having the smoothness required for a particular ultrasonic apparatus is commonly referred to as a "sonic surface." In order to produce a sonic surface the part is normally ground. While recent efforts have been made to develop ultrasonic testing techniques for parts having curved surfaces, undercuts, and the like, such techniques are time consuming and generally unsuitable for production-scale manufacturing. The easiest part to inspect by ultrasonic testing is one of a simple shape which has flat, parallel surfaces. Inherently, near net shapes produced by previously known methods have neither. Consequently, it has proven difficult to ultrasonically test such near net shapes.

BRIEF DESCRIPTION OF THE INVENTION

This invention is directed to a method for ultrasonically testing articles of near net shape which offers a unique solution to the problems which have been encountered. It has recently been discovered that near net shapes can be produced by a methodwhich includes producing a thick-walled container from a mass of fully dense and incompressible material which is capable of plastic flow at elevated temperatures.

A suitable container material is low carbon steel, such as SAE 1008 or 1010 steel. The thick-walled container employed is disclosed in co-pending U.S. patent application Ser. No. 778,009, now U.S. Pat. No. 4,142,888 granted to the inventor hereof on Mar. 6, 1979. In producing the thick-walled container, a cavity of predetermined shape is formed in the mass of material such that the walls of the container are of sufficient thickness so that the exterior surface thereof does not closely follow the contour of the cavity. It has been found that this type of container is capable of producing near net shapes having relatively close dimensional tolerances with a minimum of distortion.

The cavity of the container is filled with powder metal of desired composition. In most cases the container is evacuated by a vacuum pump prior to filling to place the cavity under a vacuum. The container is then sealed. Heat and pressure are applied to the filled and sealed container causing the container material to act like a fluid to apply a hydrostatic pressure to the heated powder metal contained in the cavity thereby consolidating the powder metal to produce a densified compact. The densified compact is then prepared for ultrasonic testing by selectively removing portions of the container to form a jacket of container material around the densified compact having the required smooth sonic surfaces. It is noted that, while the densified compact may have a complex shape including undercuts, the exterior shape of the jacket is relatively simple and is free of undercuts. Due to the shape of the jacket, the entire mass consisting of the jacket and densified part can be quickly inspected using ultrasonic testing equipment. After ultrasonic testing, the remaining container material is removed from the densified compact. Before the container material is removed, however, the densified compact may be heat treated as disclosed in U.S. patent application Ser. No. 767,522, filed Feb. 10, 1977, now U.S. Pat. No. 4,094,709.

BRIEF DESCRIPTION OF THE DRAWING

Other advantages of the present invention will be readily appreciated as the same becomes better understood by reference to the following detailed description when considered in connection with the accompanying drawing which represents a flow diagram illustrating the major steps involved in the method of the instant invention.

DETAILED DESCRIPTION OF THE INVENTION

The invention will be described with respect to a part made from Astroloy powder, a precipitation hardened nickel-base superalloy used in the production of jet engine components. The specific configuration of the part shown in the flow diagram is not intended to depict an actual production part, but is shown by way of example to illustrate a near net shape of relatively complex configuration. Similar shapes, however, are encountered in actual practice. It is to be recognized that other types of metal powder, as well as other complex shapes, may be produced in the manner disclosed herein.

As shown in Step 5 of the flow diagram, the desired near net shape, generally shown at 10, includes a disc-shaped body 11 having two annular rings 12 and 14, one of the rings extending from each side of the body. The upper ring 12 includes a radially inwardly extending flange 13 while the lower ring 14 includes a radially outwardly extending flange 15. It should be apparent that the annular flanges 13 and 15 define undercuts which cause problems in ultrasonic testing because they are relatively inaccessible by standard ultrasonic equipment and require special equipment and techniques which must be carried out by hand.

In order to produce a near net shape having the configuration shown, a thick-walled container for consolidating the powder metal is produced. The container should be made from a mass of fully dense and incompressible material which is capable of plastic flow at elevated temperatures. In the case of Astroloy powder, and other related alloys, a suitable container material is low-carbon steel, such as an SAE 1008 or 1010 steel. Low-carbon steel offers the advantages of being relatively inexpensive, readily available, and easily removed from the densified compact by machining or pickling. Other considerations which make low-carbon steel a satisfactory material for the container are that Astroloy and low-carbon steel have reasonably close coefficients of thermal expansivity and no deleterious reactions occur between the consituents of Astroloy and the low-carbon steel.

Referring to Step 1 of the drawing, a practical method for producing the container involves providing two disc-shaped pieces of steel 16 and 18. Appropriately dimensioned cavities 20 and 22 are machined in the two pieces of steel by standard machining techniques. The dimensions of the cavities are, of course, larger than the dimensions of the desired densified compact 10 to take into account the predicted amount of shrinkage which occurs as the powder densifies. While a two-piece container is shown, more complex parts may be produced by employing containers having three or more interfitting pieces. The sections 20 and 22 of the cavity are machined in the pieces of steel in a manner analogous to the fabrication of a closed die. Alternatively, the container may be cast using an expendable core to form the cavity.

In accordance with the disclosure in the aforementioned U.S. patent 4,142,888, the container is "thick-walled." By way of definition, the exterior surface of a thick-walled container does not closely follow the contour of the cavity. This insures that sufficient container material is provided so that, upon the application of heat and pressure, the container material will act like a fluid to apply hydrostatic pressure to the powder in the cavity. It has been shown that the use of a thick-walled container produces a near net shape having close dimensional tolerances with a minimum of distortion.

As shown in Step 1 of the flow diagram, each of the container parts 16 and 18 are machined to produce cavities 20 and 22 of predetermined complex shape. After machining the cavities, the internal surfaces are carefully cleaned to remove all contaminants, such as cutting fluids, oil and the like. This precaution is taken to insure the formation of a bond between the powder and the container material. In order to permit ultrasonic testing it has been found necessary that, during consolidation, the material of the container and the powder metal form one dense mass wherein the densified powder and the container material fuse together at their interface. Cutting fluids and other contaminants will prevent this fusion because they tend to form a barrier between the two metals. If the container material and densified powder are not bonded together a discontinuity is formed which will cause near total reflection of the ultrasonic waves at the container-part interface. This, of course, will prevent inspection of the interior at the densified compact.

An acceptable cleaning technique involves hot vapor degreasing using a suitable solvent, such as trichloroetheylene, to remove cutting fluids and the like. If corrosion or residue is present, the cavity walls are wire brushed prior to degreasing. In extreme cases grit-blasting is employed, but this procedure is avoided since grit particles may become embedded in the surface of the cavity walls. Such grit particles would show up as flaws during ultrasonic testing. If it is necessary to employ grit blasting, the container cavity is carefully wire brushed afterwards to remove any adhering grit particles.

As shown in Step 2, after the container parts 16 and 18 are machined and cleaned, they are joined together to form a complete container 24. This is done by a welding operation. The container parts are joined in a relatively clean environment to prevent particles from entering the cavity. Care is also taken to produce a hermetic seal between the container parts 16 and 18 so that the container can be evacuated. Poor weldments produce leaks which would permit the introduction of gas into the container during the compaction cycle. Again, it is pointed out that this process is being described with respect to Astroloy powder, an alloy which is highly reactive to oxygen. Therefore, it is desirable throughout the processing that the Astroloy powder be maintained in an inert atmosphere and, finally, under a vacuum during densification.

In the process of joining the container parts 16 and 18, the container 24 is tubulated. This is done by drilling a hole in one of the container parts for positioning a fill tube 26 which communicates with the cavity. The fill tube 26 is joined to the container part by welding. Again, care is taken to produce a hermetic seal. The container is then evacuated by connecting the fill tube 26 to a vacuum pump (not shown). After the container has been pumped down to a vacuum level of generally less than 10 microns, the container is filled with metal powder 27. Prior to filling the container, the metal powder has been degassed and maintained under a vacuum. During filling, the container 24 is rotated and vibrated to insure complete filling of the cavity to maximum tap density. After the container 24 has been completely filled with powder metal, the container is leak tested. Leak testing is done by measuring the rate of loss of the vacuum in the container. A decrease in vacuum of only a few microns per hour indicates that the container is properly sealed. After leak testing, the container is sealed by crimping and welding the fill tube 26.

At this point, the filled and sealed container is ready for the densification step. Densification of the powder metal is accomplished by heating and applying pressure to the container. Heat and pressure may be applied by using an autoclave or a hot forging press. Step 3 of the flow diagram is a schematic of an autoclave which includes a pressure vessel 28 and heating coils 30. When using an autoclave, the container 24 and contents are heated to a temperature of approximately 2050° F. and a pressure of up to 15,000 psi is applied for two hours.

Alternatively, the container 24 may be preheated in a furnace and transferred to a forging press. In order to apply pressure in a forging press, the container is restrained in a restraining ring or die cavity during pressing with the ram(s) of the press. In the case of either an autoclave or forging press, an isostatic pressure is applied to the entire exterior surface of the container 26. With regard to an autoclave, isostatic pressure is applied by the pressure medium, usually an inert gas such as argon. Isostatic pressure is also produced in the forging press by employing the restraining ring or forge die cavity. It is to be remembered that, at the densification temperatures employed, the low-carbon steel flows relatively readily under the applied pressures. Hence, even though the ram of the press applies a one-directional force (generally vertical), the container material acts like a fluid and fills the retaining cavity and reacts with an essentially equal force against all sides, ignoring the weight of the container material which is small compared to the applied force.

Applying heat and pressure to the container in the manner described causes the container material to act like a fluid thereby applying a hydrostatic pressure to the heated powder metal contained in the cavity. Since the powder contained in the cavity is not at full density, the size of the cavity will decrease. The decrease in size of the cavity can be compared to the behavior of a gas bubble in a liquid under pressure. As the pressure is increased, the hydrostatic pressure on the walls of the bubble causes the diameter of the bubble to decrease. As the bubble decreases in size the gas in the bubble is compressed. The powder in the cavity is analogous to the gas in the bubble. The powder is compressed until it reaches full density. At the temperatures and pressures involved, the container material will actually fuse with the powder if the above-mentioned cleaning precautions are taken, thus producing a unitary mass. Moreover, in the event that a container comprised of more than two parts is employed, the mating container surfaces must also be cleaned to insure that these surfaces fuse together. A small diffusion zone is produced at the interface between the container material and the densified compact. This diffusion zone is very small and is normally limited to two atomic diameters. However, the two materials are intimately bonded together at their interface.

After hot compaction, the container is removed from the autoclave 20 or forging press and allowed to cool.

The next step, Step 4 of the flow diagram, involves preparing the densified compact for ultrasonic testing. This is done by partially removing portions of the container material in a selective and predetermined manner. As a minimum, the two opposite faces 29 and 31 are machined so that they are parallel. The surfaces must also be ground to a smoothness which is specified for the particular ultrasonic equipment employed. In other words, "sonic surfaces" are machined on the container. By way of example, when consolidation is carried out in an autoclave, the two opposite faces 29 and 31 of the container become concave. The machining operation flattens the two surfaces and make them parallel. The machining operation also leaves a surface at the required smoothness for ultrasonic testing. Once the faces 29 and 31 are flat and parallel, ultrasonic testing can be performed using standard testing techniques.

Ultrasonic testing will indicate the presence of flaws in the container material as well as in the densified compact. Obviously flaws in the container material are ignored. Since the ultrasonic testing equipment is capable of measuring the distance of the flaw below the surface, it is normally possible to discriminate between flaws occurring in the container and flaws occurring in the densified compact. When a flaw occurs near the the interface of the densified compact it may be difficult to determine whether the flaw is in the densified compact or the container. In such a case the container material can be removed from the suspected area and the densified compact is again ultrasonic tested.

By employing the container to form an ultrasonic shape, ultrasonic testing can thus be carried out quickly and effectively. Even though it may still be desirable to again test the final part by ultrasonics, this method permits an inexpensive and quick testing of the quality of the densified compact so that defective compacts can be eliminated at an early stage in the processing before additional processing costs are incurred.

There are situations in which it is desirable to remove a greater amount of container material. For example, the container material can also be used as a protective jacket during heat treating to prevent warpage of thin sections and to promote uniform cooling rates. When the container is used for this purpose more container material is removed. For example, the container material may be machined to produce a jacket 32 around the densified compact 34 as shown in Step 4 of the drawing. The upper and lower surfaces of the jacket 32 are machined flat and parallel so that the composite can be ultrasonically tested.

After ultrasonic testing, the jacket of container material is removed from the densified compact. This may be accomplished by etching in a suitable acid bath. The etchant removes the ferrous base metal, but will not attack the nickel base metal. After etching the densified compact may be grit-blasted to remove any residue. Alternatively, the jacket of container material may be removed by machining.

While the container material is sacrificed in the process described, it is pointed out that the cost of low-carbon steel is a fraction of the cost of superalloy powder, such as Astroloy.

The near net shape shown in Step 5 is then ready for further processing, typically, final machining. It should be apparent, however, that a significant number of previously required intermediate steps have been eliminated by producing a near net shape. Moreover, problems associated with producing and heat treating a near net shape have been reduced.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that the invention may be practiced otherwise than as specifically described herein and yet remain within the scope of the appended claims.

I claim:

1. A method of forming and sonic testing powder metal articles comprising the steps of producing a thick-walled container by forming a cavity of predetermined complex shape in a mass of suitable container material such that the walls of the container are of sufficient thickness so that the exterior surface thereof does not closely follow the contour of the cavity, cleaning the cavity to remove contaminants, filling the cavity with powder metal and sealing the container, applying heat and pressure to the container to consolidate the powder metal to produce a densified compact, preparing the densified compact for sonic testing by selectively removing portions of the container to form sonic surfaces on the jacket of container material around the densified compact, sonic testing the densified compact and completing removal of the container material.

2. A method of sonic testing articles of powder metal made by hot isostatic pressing in a thick-walled container comprising the steps of preparing the composite thick-walled container and article for sonic testing by machining sonic surfaces in the exterior surface of the thick-walled container and thereafter sonic testing the article through the walls of the container.

* * * * *